United States Patent [19]

Bucalo

[11] 4,232,673

[45] Nov. 11, 1980

[54] METHOD FOR COLLECTING AND PROCESSING BODY FLUIDS

[76] Inventor: Louis Bucalo, 155 Roberts St., Holbrook, N.Y. 11741

[21] Appl. No.: 603,432

[22] Filed: Aug. 11, 1975

[51] Int. Cl.² ........................................... A61B 10/00
[52] U.S. Cl. ..................................... 128/769; 128/285
[58] Field of Search ............ 128/2 F, 2 W, 2 R, 260, 128/275, 1 R, 285, 769; 195/103.5 R, 139, 140

[56] References Cited

U.S. PATENT DOCUMENTS

| 599,955 | 3/1898 | Beach | 128/285 |
|---|---|---|---|
| 1,502,503 | 7/1924 | Hollrigl | 128/285 |
| 2,905,169 | 9/1959 | Nieburgs | 128/2 W |
| 3,057,344 | 10/1962 | Abella et al. | 128/2 F |
| 3,308,039 | 3/1967 | Nelson | 128/2 W X |
| 3,315,660 | 4/1967 | Abella | 128/2 F |
| 3,319,622 | 5/1967 | Shiner | 128/2 F |
| 3,485,235 | 12/1969 | Felson | 128/2 F |

*Primary Examiner*—Kyle L. Howell
*Attorney, Agent, or Firm*—Steinberg and Blake

[57] ABSTRACT

Methods for purposes such as obtaining information pertaining to human beings or other animals having body cavities wherein fluids from which desired information can be derived are at least temporarily present. A means for collecting a body fluid is introduced into the body cavity and left therein for a time sufficient to provide for collection of a quantity of fluid suitable, for example, for subsequent analysis. The fluid collected by the collecting means is enclosed in an enclosure which can then be transmitted to a laboratory or the like for subsequent analysis of the fluid.

25 Claims, 16 Drawing Figures

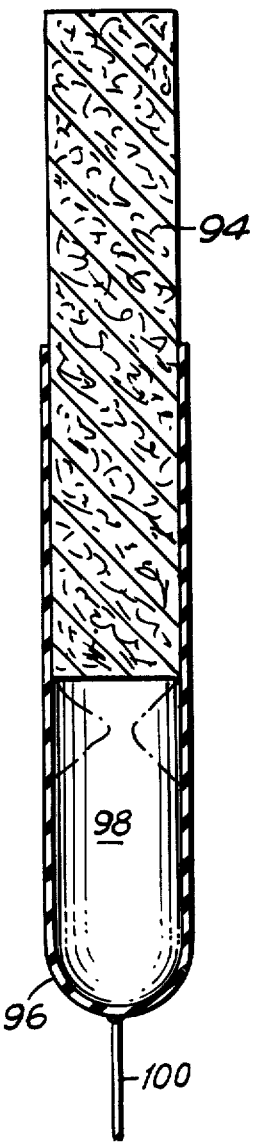
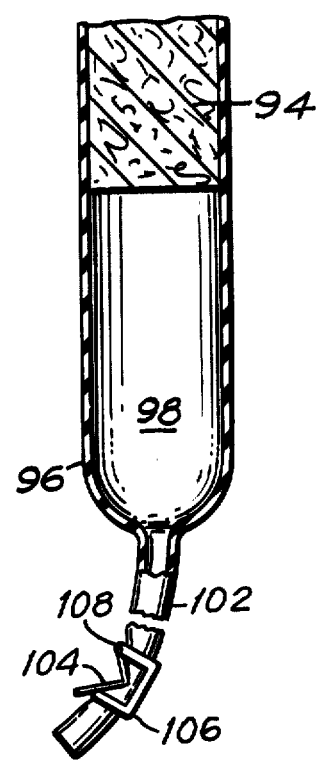
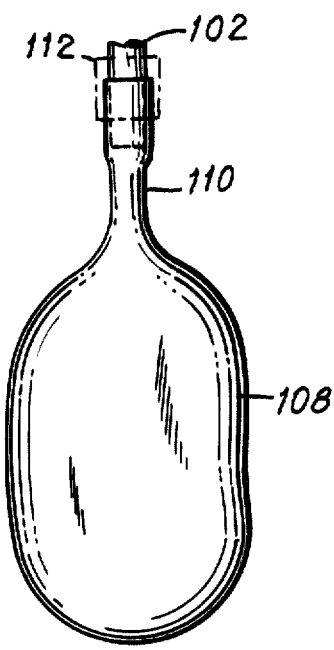
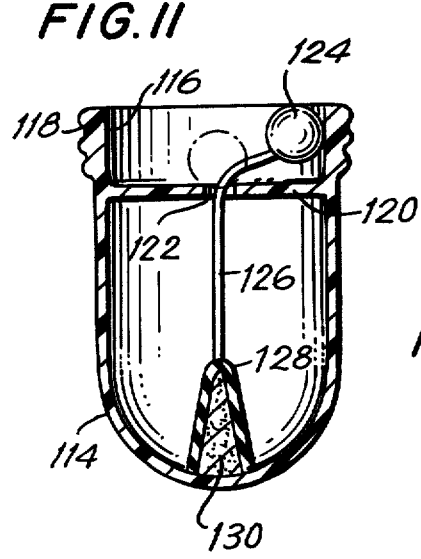
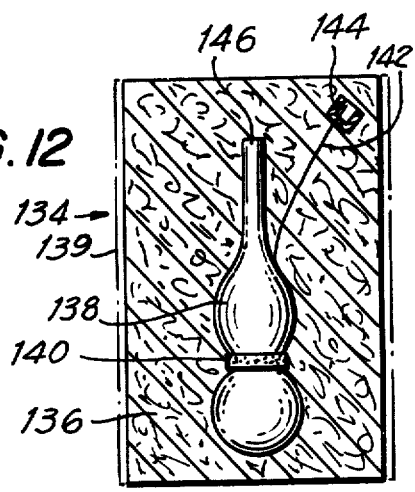
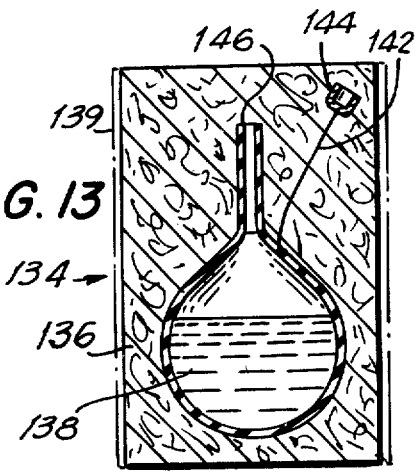

METHOD FOR COLLECTING AND PROCESSING BODY FLUIDS

BACKGROUND OF THE INVENTION

The present invention relates to methods for collecting fluid in a body cavity, particularly the vagina, of a human being or other animal and for then treating the collected fluid in a predetermined manner.

Presently known methods involve certain disadvantages and inconveniences. For example where a physician feels that a patient may have a certain disease, it is common to take a swab and transmit the specimen removed by the swab to a laboratory for analysis. These procedures are not highly reliable because the removed specimen is of a limited magnitude. In connection with normal menstrual flow of healthy female adults, considerable inconviences involved in the use of conventional tampons and sanitary napkins inasmuch as items of this type must be frequently changed.

In addition, where the presence or absence of certain diseases are to be determined, with conventional methods there is not only a lack of reliability as referred to above but in addition there is an unavoidable and undesirable delay in determining the results.

SUMMARY OF THE INVENTION

It is accordingly a primary object of the present invention to provide methods for avoiding the above drawbacks.

In particular, it is an object of the present invention to provide methods for collecting body fluids and enclosing the latter in a manner suitable for analysis of the collected body fluids while at the same time avoiding the possibility of causing undesirable multiplication of microorganisms in the body.

In addition it is an object of the present invention to provide methods of this type which will assure a rapid reliable growth of suspected microorganisms under ideal conditions even before a specimen reaches the location where an analysis thereof is to be made.

It is furthermore an object of the present invention to provide methods of the above type which will cause no discomfort to the human being or other animal from whom the body fluid is taken.

In addition it is an object of the present invention to provide a method for collecting menstrual fluid either for purposes of subsequent analysis or for the purpose of eliminating the menstrual fluid, in such a way that disadvantages inherent in conventional methods of this type are avoided.

According to the invention there is introduced into a body cavity a means for collecting body fluid therein while the latter means remains in the body cavity for a length of time sufficient to provide for collection of a quantity of fluid suitable for subsequent analysis. The thus-collected fluid is enclosed in a suitable enclosure which is transmitted to a laboratory or the like where subsequent analysis takes place. The enclosure which receives the body fluid may in some cases be situated in the body cavity together with the means for collecting the body fluid, and such an enclosure may be either manually or automatically closed after a suitable quantity of fluid has been collected therein. In addition, it is possible to release to the interior of the enclosure after a suitable quantity of fluid has been collected therein an agent which will have a desired effect with respect to the collected body fluid, such an agent being, for example, a broth in which microorganisms will rapidly grow. In connection with menstrual flow, according to the invention there may be situated in the vagina a means which will collect the menstrual fluid so that the menstrual fluid can either be simply discarded or collected in a suitable container which can be sent to a laboratory for analysis of the menstrual fluid.

BRIEF DESCRIPTION OF DRAWINGS

The invention is illustrated by way of example in the accompanying drawings which form part of this application and in which:

FIG. 8 is a schematic illustration of a further embodiment of the invention;

FIG. 9 shows a variation of the embodiment of FIG. 8 particularly suitable in connection with menstrual flow;

FIG. 10 shows yet another variation of the embodiment of FIG. 9; FIG. 11 is a sectional elevation schematically illustrating yet another embodiment of the invention;

FIG. 12 shows a still further embodiment of the invention;

FIG. 13 illustrates the condition taken by the embodiment of FIG. 12 after the embodiment of FIG. 12 has remained in a body cavity for a certain interval;

DESCRIPTION OF PREFERRED EMBODIMENTS

Figure 1:
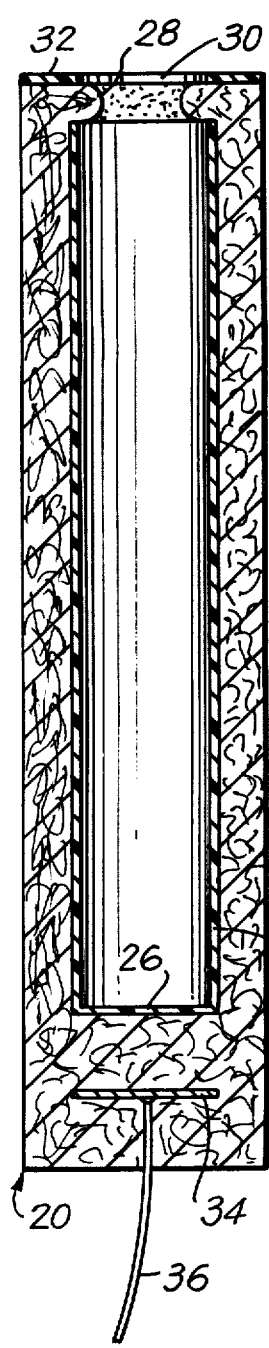
FIG. 1 is a schematic illustration of one possible embodiment of an apparatus for carrying out a method according to the invention.

Referring now to FIG. 1, there is schematically illustrated therein an apparatus 20 for carrying out one embodiment of the method of the invention. This apparatus 20 may include an outer cushioning body 22 which may be absorbent or non-absorbent. This body 22 will enable the apparatus 20 to be situated comfortably within a body cavity such as the vagina, the rectum, or the like. The cushion 22 can be made of cotton wadding, or any soft plastic material which if it is desired to be absorbent can have the characteristics of a sponge.

Situated within the cushion 22 is an enclosure means 24 in the form of a container having its bottom end, as viewed in FIG. 1, closed by a suitable transverse wall 26 of the container 24. The container 24 is open at its top end as viewed in FIG. 1. Extending across this open top end of the container 24 is a wall 28 which forms part of a means for collecting fluid which is present in the body cavity. This wall 28 forms a part of the cushion 22 and extends across the open end of the container 24 while being formed with an opening 30 through which collected fluid will enter into the interior of the container 24 to remain therein. The nature of the opening 30 is such that while fluid will enter through the opening 30 into the container 24 it is highly unlikely to be discharged out of the container 24 through the opening 30 back into the body cavity. In order to promote collection of fluid through the collecting means 28 into the interior of the container 24 the outer end face of the cushion 22, which is the upper end face thereof as viewed in FIG. 1, is covered with a barrier layer 32 formed of any suitable plastic or the like which adheres to the cushion 22 and which is impervious to the fluid which is to be collected so that if the fluid engages the barrier layer 22 it will simply flow across the latter to the opening 30 of the collecting means 28 so as to be collected thereby and introduced into the container 24.

As an optional feature, the cushion 22 may have embedded therein a plate, rod, pin, or the like 34 to which one end of a pull-string 36 is attached as illustrated so that through this optional pull-string 36 it is possible to readily remove the apparatus 20 from the body cavity after it has remained therein for a length of time sufficient for collection of a suitable quantity of fluid in the container 24.

Upon such retraction from the body cavity the opening 30 can be closed as by placing a suitable tape across the barrier layer 32, or if desired the entire apparatus 20 can simply be situated in a suitable bottle or the like which can be closed and shipped with the apparatus 20 to a laboratory where the fluid in the container 24 can be tested.

It is also possible to situate in the container 24 prior to insertion of the apparatus 20 into the body cavity a suitable preservative or stabilizer such as an antibiotic or citric acid so that the received body fluid can be influenced in a manner desirable for the subsequent analysis thereof.

Figure 2:
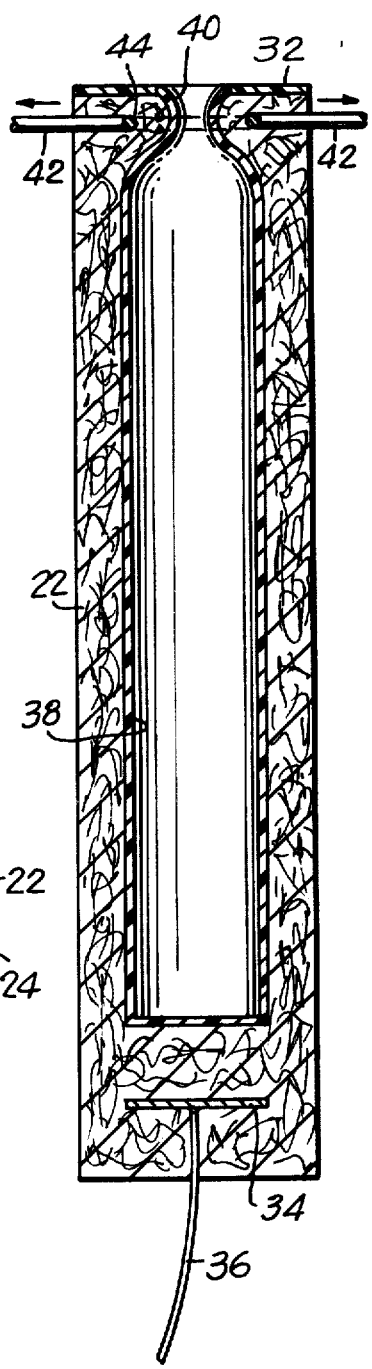
FIG. 2 is a schematic illustration of a further embodiment of an apparatus according to the invention.

The embodiment of FIG. 2 is substantially identical with that of FIG. 1, the difference being that the container 24 which forms the enclosure means of FIG. 1 is replaced by a container 38 having an upper flexible tubular wall portion 40 which initially has an open condition, as illustrated in FIG. 2, so that this wall 40 forms the means for collecting the body fluid. The wall 40 extends up to the barrier layer 32, and the entire enclosure 38 together with the collecting means 40 are situated in the cushioning element 22 which may be absorbent or non-absorbent as described above and which may have a suitable pull-string 36 connected thereto if desired. Also within the container 38 it is possible to situate a suitable preservative such as an anitbiotic or the like, as referred to above in connection with FIG. 1.

With the embodiment of FIG. 2, after the device has been removed from the body cavity it is possible to close the opening 40. For this purpose a drawstring is embedded in the element 22 with a portion surrounding the wall 40 which has the opening through which the fluid enters. This drawstring can have a loop extending around the wall 40 and having opposed free ends 42 accessible to the operator for pulling so as to tightly close the loop around the wall 40 for shutting the opening formed thereby. In this way this manual closure means formed by the drawstring 44 can be manipulated to tightly close the container 38 so as to render the latter suitable for transmittal to a laboratory or the like where analysis of the collected fluid will take place.

Figure 3:
FIG. 3 is a schematic illustration of a still further embodiment of the invention.

According to the variation of the invention which is illustrated in FIG. 3, the apparatus includes an outer cushioning element 46 which is optional inasmuch as the container 48 which extends partly into the cushioning element 46 may itself be made of a relatively soft film of plastic material such as polyethylene or the like which can comfortably be situated in a body cavity. Suitable plastics may have corrugated or bellows-types of wall structures giving the container 48 a flexibility rendering it highly suitable for comfortable situation in a body cavity without the use of the optional cushion 46.

Figure 4:
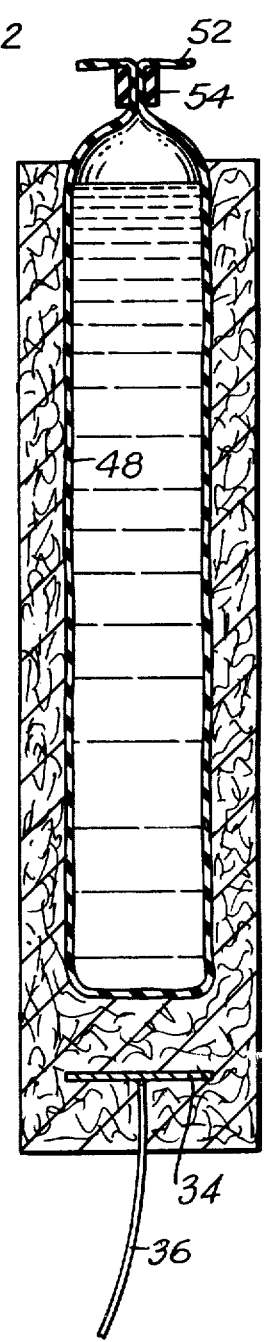
FIG. 4 shows the structure of FIG. 3 after the container with fluid therein has been closed.

The plastic material which is used for the enclosure means 48 has, a viewed in FIG. 3, an upper open end 50 forming the collecting means for collecting the fluid which is enclosed within the enclosure means 48. The flexible material of the enclosure 48 has in the illustrated example an outwardly extending flange portion 52. Adjacent the flange 52 and beyond an end of the cushion 46 there is a surrounding elastic band 54 which forms a closure means for automatically closing the opening formed by the collecting means 50 so as to close off the interior of the container 48 for retaining fluid therein which has been previously collected. In order to maintain the elastic band 54 in its expanded condition illustrated in FIG. 3 the inner surface of the upper open end region of container 48 which forms the collecting means 50 surrounds and is engaged by a substantially rigid ring 56 which is strong enough to maintain the elastic 54 in the stretched condition illustrated in FIG. 3. The ring 56 may be in the form of a dissolvable material which automatically dissolves when engaged by the body fluid, such materials being well known in the case of dissolvable sutures and the like, for example. Thus the dimensions of the ring 56 is such that it will reliably retain the collecting means 50 in the condition illustrated in FIG. 3 for a time interval sufficient for reliable collection of a suitable quantity of fluid in the container 48. When the ring 56 dissolves sufficiently either as a result of contact by the body fluid and/or as a result of exposure to the temperature prevailing in the body cavity, the ring 56 will give way so as to permit the elastic band 54 to contract to the condition shown in FIG. 4. It will be noted that this embodiment also has an optional pull-string 36 which enables the apparatus to be conveniently withdrawn from the body cavity. If desired the ring 56 can be made of a suitable plastic which does not dissolve but which has attached thereto an unillustrated string so that the operator by engaging the pull-string 36 and a string attached to a plastic or even metal ring 56 can retract the latter out of the open end 50 which forms the collecting means, thus permitting in this way the elastic 54 to contract to the condition shown in FIG. 4 for closing the container. Thus with such an embodiment it will not be necessary to enclose part of the dissolved ring 56 in the interior of the container and by manual operations it is possible to close the container 48 in the manner illustrated in FIG. 4, rendering the structure of FIG. 4 suitable for transmittal to a laboratory where the fluid in the container 48 will be analyzed. Of course in this case also within the container 48 there may be situated an agent such as a preservative, an antibiotic, a growth means, or the like.

Figure 5:
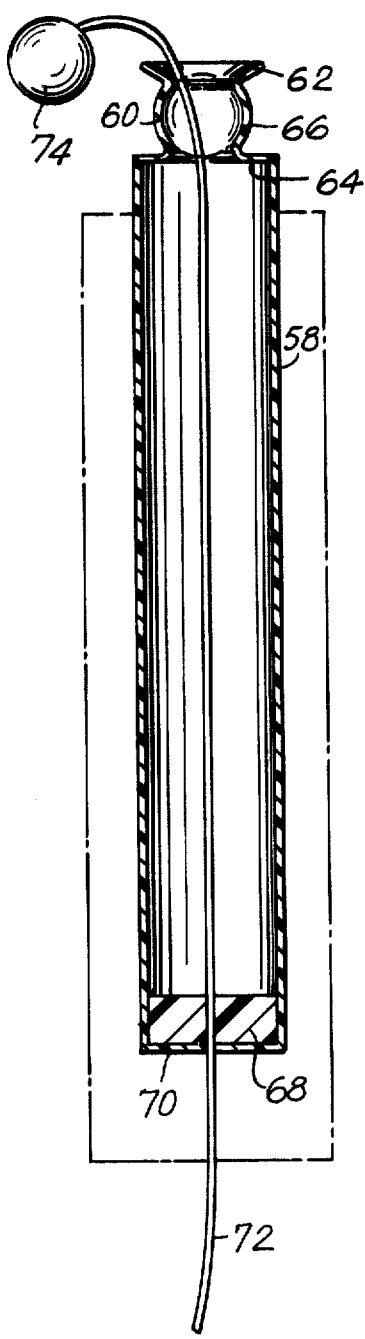
FIG. 5 shows a further embodiment of the invention according to which it is possible to close manually a container which receives a collected body fluid.

The embodiment which is illustrated in FIG. 5 also has an enclosure means formed by a container 58 made of a suitable relatively soft plastic material which can be comfortably situated in any body cavity without the use of an optional cushion which is shown in phantom lines in FIG. 5. At its upper end, as viewed in FIG. 5, the container 58 has the collecting means 60 formed by the illustrated neck of the container 58 which extends from a wall portion which extends across the interior of the container 58 and then merges into the neck 60 which has an outer flared end 62 and next to the wall portion 64 an intermediate portion 66 which has an inner concave circular surface as illustrated. At the bottom end of the container 58, as viewed in FIG. 5, is a body 68 of a suitable plastic material which directly engages the bottom wall 70 of the container 58. Extending slidably and fluid-tightly through the plastic 68 and the wall 70 is a pull-string 72 the upper end of which is connected with a closure ball 74 which normally has the position illustrated leaving the collecting means 60 in the open condition enabling collection of fluid which automatically enters into the container 58. When it is desired to terminate the collection of fluid the operator will pull the string 72 so as to displace the closure member 74 to the dot-dash line sealed position illustrated in FIG. 5 closing the collecting means 60 so that no more fluid can enter into the container 58, and further pulling of the string 72 may serve to extract the device of FIG. 5 from the body cavity. The container 58 is now in a condition for transmittal to a laboratory for analysis of the collected fluid. Of course in this case also it is possible to situate in the interior of the container any desired agent such as a suitable preservative such as an antibiotic or the like.

Figure 6:
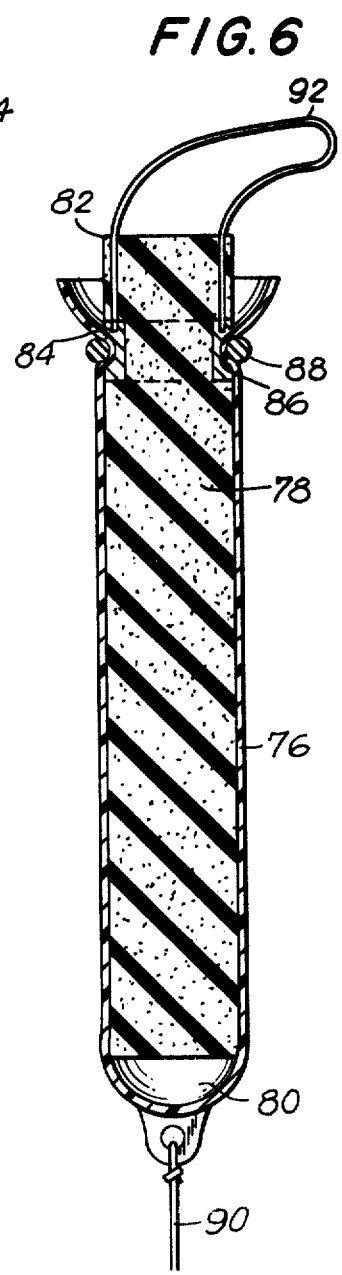
FIG. 6 is a schematic illustration of yet another embodiment of the invention for collecting and enclosing a body fluid.
Figure 7:
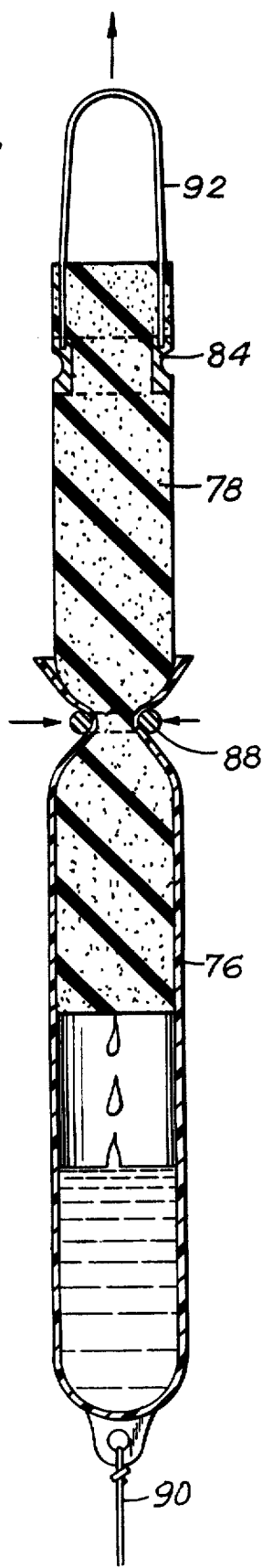
FIG. 7 illustrates how the structure of FIG. 6 is operated.

Referring now to FIGS. 6 and 7, there is illustrated therein an embodiment of the invention which includes an outer enclosure means 76 in the form of a flexible non-porous bag made of a suitable plastic such as polyethylene or the like. The flexible material of the container or enclosure means 76 surrounds a collecting means which in the illustrated embodiment operates by capillary action and takes the form of a foam plastic such as a plastic made of polyurethane and having relatively large cells so that the fluid can freely pass through the open cells of the collecting means 78 into the interior of the enclosure means 76. It will be noted that the enclosure means 76 has below the collecting means 78 a free space 80 into which the fluid can flow from the means 78. On the other hand the means 78 extends to the exterior of the enclosure means 76 so as to engage directly with the fluid which is to be collected and which by capillary action become sucked into the means 78 to flow through the latter into the space 80. Of course, the spongy material of the collecting means 78 is compressible. Adjacent its outer end 82 which engages the body fluid the means 78 is fixed as by suitable adhesive with a surrounding relatively rigid ring 84 which in turn is surrounded by part of the flexible film which forms the bag 76, and the ring 84 is formed with an outer groove 86 into which part of the bag 76 is pressed by a circular elastic band 88, as illustrated. The lower end of the flexible bag 76 has a pull-string 90 attached thereto while the ring 84 has an additional pull-string 92 attached thereto.

With this embodiment of the invention after the structure shown in FIG. 6 has remained in the body cavity for a time sufficient for collection of a suitable quantity of fluid, the pull-string 90 is manipulated to extract the structure of FIG. 6 from the body cavity. Then the pull-string 92 is pulled away from the pull-string 90 by the operator, in the manner shown in FIG. 7. The result is that the ring 84 is displaced together with the collecting means 78 away from the enclosure means 76 while at the same time the elastic band 88 contracts to compress the spongy means 78 in the manner illustrated in FIG. 7. During the continued withdrawal of the means 78 from the container 76 fluid in the cells of the means 78 will be extracted therefrom to be received in the container 76, and upon completion of the withdrawal of the means 78 from the container 76 the elastic 88 will automatically close the container 76 so that the latter can then be transmitted to a suitable laboratory where the collected fluid will be analyzed. Of course with this embodiment also it is possible to situate an optional preservative in the container 76, or another suitable agent such as an antibiotic preservative may be situated in the container 76, either during or after collection of the fluid.

An embodiment of the invention which is similar to that of FIG. 6 but which is considerably simplified as compared to FIG. 6 is illustrated in FIG. 8. This particular embodiment is suitable especially for collection of menstrual or other vaginal fluid. According to FIG. 8 the collecting means takes the form of a tampon 94 which may have the construction of a conventional tampon as utilized during menstrual flow. However according to the invention, a part of the tampon extends into a flexible enclosure means 96 which may be a simple flexible bag or the like made of a thin polyethylene film which is impervious to liquid. The diameter of the enclosure means 96 is such that it will grip the exterior surface of the tampon 94 with sufficient friction to retain the components in the position with respect to each other illustrated so that, for example, the tampon 94 will extend half into and half outside of the container 96 while the latter will have beyond the tampon 94 a free interior space 98 capable of receiving the fluid. A pull-string 100 may be attached to the bottom end of the enclosure 96 for conveniently extracting the latter from the body cavity such as the vagina. With this embodiment the assembly of the components 94 and 96 is relatively soft and flexible so that it will become deflected and squeezed as a result of body movements, so that these normally occurring body movements will result in squeezing of fluid out of the tampon 94 into the space 98 of the enclosure means 96. In this way it is possible with the embodiment of FIG. 8 either simply to extend the interval during which a conventional tampon may be used or if desired the tampon 94 together with the bag 96 may be placed in a suitable bottle or the like which is closed and transmitted to a laboratory for analysis of the collected fluid. Of course in this latter event it is possible to situate in the space 98 a suitable preservative such as an antibiotic or the like. As is shown in phantom lines in FIG. 8, the bag or enclosure means 96 may be made of a stretchable material in such a way that just below the tampon 94 it will have a narrow neck portion to retard any flow of collected fluid from the space 98 back to the tampon 94. Thus, the plastic which forms the bag 96 may be molded in such a way that it will have when connected with the tampon 94 the narrow neck as illustrated.

According to the embodiment of the invention which is illustrated in FIG. 9, the collecting means 94 may be identical with that of FIG. 8 while the enclosure means 96 includes not only the flexible bag of polyethylene film or the like as described above in connection with FIG. 8 but also an elongated tubular member 102 which is flexible and which is joined to the bottom end of the enclosure 96 so that fluid from the tampon will enter not only the space 98 but also the flexible tube 102. The flexible tube 102 can extend to the exterior of the body where it carries a valve means 104 in the form of a pinch valve or the like. For example the tube 102 can extend through a conventional enema clip or similar structure having a short metal sleeve 106 part of which is cut away to receive a flexible leaf spring 108 which normally assumes a position pinching the flexible tubular component 102 so as to close the latter. The individual who has the tampon and container 96 as well as part of the tube 102 situated in the vagina can from time to time manipulate the spring 108 so as to open the valve means 104 and thus release the collected fluid, and the collected fluid can either be discarded or introduced into a container for transmittal to a laboratory for analysis. Thus, with an embodiment as shown in FIG. 9 it is possible to extend considerably the interval during which a tampon 94 may be retained in the vagina.

According to the embodiment of the invention which is illustrated in FIG. 10 the outer end region of the tube 102, which may or may not have the valve means 104 of FIG. 9 attached thereto, is releasably connected with a flexible container 108. Thus, the flexible container 108 has a tubular extension 110 which can be slipped over the outer end of the tube 102 and releasably retained thereon as by a surrounding piece of adhesive tape 112. The container 108 can also be made of a suitable plastic film such as polyethylene and it can conveniently be carried at the exterior of the body in any suitable way. For example it can be attached to an undergarment. For example a pocket made of any suitable fabric may be provided for receiving the container 108 and such a pocket may be pinned to an undergarment for conveniently situating the container 108 at the exterior of the body. With such an arrangement during menstrual flow the menstrual fluid will accumulate within the container 108 which need only be changed from time to time for another container by removing the tape 112 and replacing one container 108 with another container 108. A removed container 108 can of course be transmitted to a laboratory for analysis of the fluid or it may simply be discarded.

In this way it is possible to extend considerably the interval during which an individual tampon 94 will be used. With this particular embodiment of the invention, which is to say any of the embodiments of FIGS. 8-10, there will be situated in the container 96 or 108 or both a suitable antibiotic, for exmaple, which will function to kill microorganisms which otherwise might cause undesirable results. In addition if the container 108 is to be transmitted to a laboratory it may contain a suitable preservative or the like which may be introduced either before or after the fluid is collected.

Referring now to FIG. 11, there is shown therein a flexible fluid-impervious enclosure 114 made of any suitable plastic material and capable of being introduced into the vagina while having dimensions so as to be comfortably situated in the vagina. As its outer wall adjacent its open end 116 the enclosure 114 has a circular grooved or corrugated surface portion 118 which engages the wall of the vagina to comfortable retain the enclosure 114 therein. At the region of its open end 116 this enclosure 114 has fixedly connected thereto a transverse wall 120 which is formed with a small opening 122 through which fluid can enter into the interior of the enclosure 114 so that the wall 120 form the means for collecting the fluid which is enclosed within the enclosure means 114 of this embodiment. Any suitable preservative such as an antibiotic or the like may be situated in the interior of the enclosure 114 beneath the wall 120. The exterior surface of the wall 120 can pivotally carry a suitable flap which can be turned so as to close the opening 122 after fluid has been collected in the enclosure 114, and the latter can if desired be provided with an exterior pull-string to facilitate extraction of the enclosure 114 from the vagina. In the example illustrated in FIG. 11 a closure member in the form of a suitable small ball 124, for example, is connected to a flexible string 126 which extends through the opening 122 without substantially obstructing the latter. Within the container 114 the string 126 is attached to an elastic band 128 which is fixed at its ends 130 in any suitable way to the wall of the enclosure 114. Initially the elastic band 128 is stretched over a body 130 of a material such as gelatin or the like which dissolves when engaged by body fluid.

Thus, as fluid which enters through the opening 122 of the collecting means 120 is collected in the enclosure 114, this fluid engages the body of material 130 to dissolve the latter and after a given time the elastic 128 will contract to automatically pull through the string 126 the closure member 124 into a position closing the opening 122, and thus the interior of the container 114 will be closed so that the container 114 can then be transmitted to a laboratory or the like for analysis of the collected fluid. Of course, as pointed out above, any suitable preservative such as an antibiotic or the like can be situated in the enclosure 114 before or after collection of fluid therein.

According to the embodiment of the invention which is illustrated in FIGS. 12 and 13, the device 134 includes a tampon 136 made of any suitable absorbent material and having dimensions suitable for insertion into a body cavity such as the vagina. Within the tampon 136 is embedded a flexible container 138 made of a plastic such as polyethylene, for example. The container 138 has a springy wall structure so that the container 138 seeks to assume the configuration illustrated in FIG. 13. However, initially the container 138 is surrounded at an intermediate portion by a meltable or dissolvable band 140 which maintains the container 138 in the deformed condition illustrated in FIG. 12. Also the container 138 has fastened thereto a string 142 carrying a closure cap 144 which can be placed over the top open end 146 of the container 138. Thus the entire container 138 together with the meltable or dissolvable band 140 and the cap 144 together with the string 142 are embedded within the absorbable body 136 which is introduced into the body cavity. As fluid is absorbed by the element 136, this fluid will after a time come into engagement with the band 140 to cause the latter to melt or dissolve with the result that the container 138 will expand to the condition shown in FIG. 13. Because the tampon 136 is relatively soft, it may be desirable in some cases, as an alternative, to provide the tampon 136 around its exterior cylindrical surface with a stiffener means 139. This stiffener means 139 may, for example, take the form of a yieldable plastic sleeve made of any suitable plastic material such as polyethylene and this sleeve may be corrugated if desired so as to add to the relative stiffness thereof without preventing yielding of the plastic sleeve and the tampon 136 so that it can readily adapt itself to the curvature of the body passage, for example. Thus, with such a stiffening means 139 the tampon 136 cannot be unduly compressed by flexing and movement of the body cavity in which the tampon is located with an undesirable effect on the container 138. Moreover, with sleeve 139, shown in phantom lines in FIGS. 12 and 13 since it is only an alternative capable of being added to the tampon 136 if desired, the fluid which is absorbed by the tampon cannot enter through the side of the tampon where the sleeve 139 is located. Instead the fluid can only enter through the front end of the tampon shown at the upper part of FIGS. 12 and 13. The result is that proper collection of fluid 138 is assured because the fluid absorbed by the tampon must travel down the tampon from the top thereof to the elevation of the band 140 in order for the latter to be contacted by the fluid and to dissolve as described above. Without the sleeve 139 the fluid could also be absorbed laterally through the side of the tampon to reach the band 140 relatively quickly and thus providing the possibility of expansion of the container 136 before there is in the tampon a sufficient amount of fluid to be collected into the container through the top end 146 thereof. Thus, a sleeve such as the sleeve 139 will function not only to prevent undesirable collapse or compression of the tampon itself but also such a sleeve will act as a barrier to force the fluid to enter only through the front end of the tampon so as to assure proper fluid collection.

Of course, sleeve 139 is referred to only as an example. Other constructions are possible for the same purpose. For example the exterior cylindrical side surface of the tampon may be impregnated with a suitable stiffener, such as silicone rubber, which also will provide the tampon with the required yieldability while at the same time preventing undesirable collapse or flattening thereof and also acting as a barrier to assure absorption only through the front end of the tampon.

Therefore, when the band 140 is contacted by the fluid so as to dissolve, the container 138 will expand to change from the condition shown in FIG. 12 to the condition shown in FIG. 13. During such expansion the increase in the volume of the container will suck fluid from the body 136 into the interior of the container 138. When the tampon 136 is removed from the body cavity the container 138 can be removed from the tampon, and now the cap 144 is available to be placed over the open end 146 of the container 138 to close the latter and enable it to be transmitted to a laboratory or the like where the collected fluid will be analyzed. Of course in this case also the container 138 may be provided before or after collection with any preservative or the like.

Figure 14:
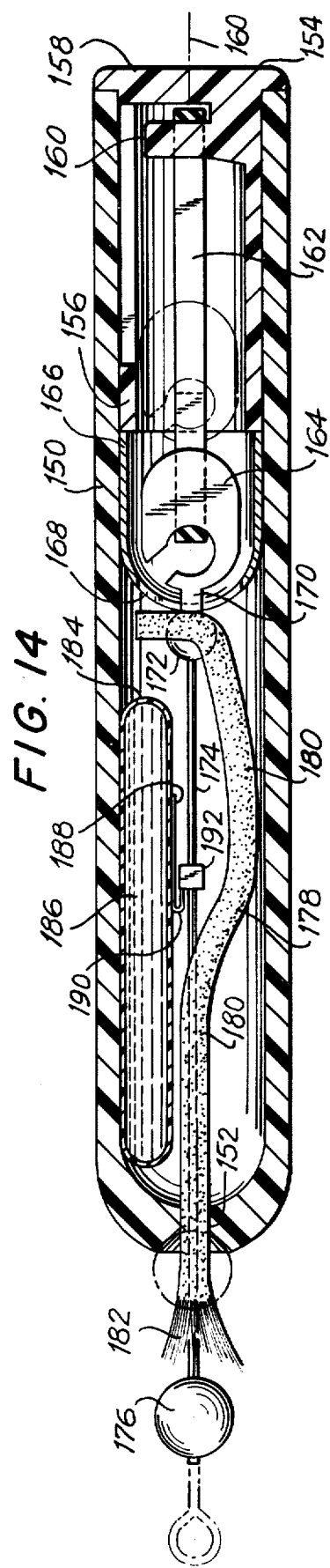
FIG. 14 is a longitudinal sectional illustration of yet another embodiment of the invention.

Referring now to the embodiment of the invention which is illustrated in FIG. 14, there is illustrated therein an elongated container 150 which is made of a relatively soft and flexible material. For example the container 150 may be made of polyethyelene. The elongated tubular container 150 forms the enclosure means for enclosing the collected fluid. The left end of the container 150 is formed with an opening 152, this left end being curved so as to have the substantially hemispherical configuration illustrated. The outer end of the opening or bore 152 tapers as illustrated for a purpose referred to below.

The opposed end of the elongated tubular container 150, which is soft enough to be comfortably received in a body cavity, is open. This right end is closed by a separate closure member 154 which can be made of a suitable plastic which is bonded to the tubular container 150 so as to tightly close the right end thereof. This member 154 is itself in the form of a hollow tubular member which at its right end completely closes the container 150 while at its left end it has a ring-shaped portion 156 for a purpose referred to below. Next to the end wall portion 158 of member 154 the latter has an integral projecting portion 160 onto which one end of an elastic band 162 is hooked. The elastic band is endless and at its other end is received in a hook member 164 which also may be made of a suitable plastic.

The ring shaped portion 156 is engaged by one end of a hollow cup-shaped member 166 made of gelatin, agar, paper, or any material which can dissolve or become soft by engagement with the collected fluid or which in response to the temperature prevailing in the body will become soft and give way from the configuration illustrated in FIG. 14. This member 166 has a tubular portion directly engaging the ring 156 and extending along the inner surface of the container 150 while terminating in a hemispherical portion formed with an elongated slot 168 through which a flat band-shaped portion 170 of a plastic extension of the hook member 164 extends. The member 164 is a simple flat body of plastic formed with a substantially keyhole-shaped slot which receives the end of the elastic band 162 as illustrated. The flat portion 170 which extends through the slot 168 is integral with a ball member 172 also made of a suitable plastic in the same way as the parts 164 and 170, and this ball member 172 has a diameter too large to pass through the slot 168 so that this construction maintains the elastic band 162 in its tensioned stretched condition illustrated in FIG. 14.

The ball 172 is integral with an elongated tie-rod or retractor element 174, which simply takes the form of an elongated filamentary body of the same plastic material as the elements 172, 170, and 164. This elongated filamentary retractor element 174 extends freely through the opening 152 to the exterior of the container 150 where the filamentary element 174 is integrally formed with a sealing ball member 176 which serves to close the opening 152 in a manner described in greater detail below. Initially the sealing or closure member 176 is situated well beyond the opening 152 in a manner illustrated in FIG. 14.

The means for collecting the fluid in the embodiment of FIG. 14 also operates by capillary action and takes the form of an elongated wick 178 which can be made of a suitable braided filamentary cotton or other material. It is possible, however, also to make the wick in the form of a simple capillary tube. In some cases the opening alone may be sufficient for collection, so that a wick is unnecessary. An elongated portion 180 of the wick passes through the opening 152 as illustrated. The tie-rod or retractor element 174 also extends along the interior of this portion 180 of the wick. At its outer end which is situated outwardly beyond the container 150 the wick has a frayed end 182 for facilitating collection of the body fluid. Between the ball member 172 and the portion 180 of the wick has a portion 182 which is curved as illustrated so as to be separated from the interior portion of the filamentary element 174 where it is joined to the interior ball member 172, and the right free end of the wick 178 is situated as illustrated around part of the ball member 172 and next to the curved end of element 166 which is formed with the slot 168.

In accordance with a further feature of the invention there is joined by any suitable adhesive or the like to the interior surface of the container 150 an inner flexible bag 184 which contains in its interior an agent which is to be released to the interior of the container 150. This inner bag 184 or the like may contain a preservative such as an antibiotic agent, or a suitable broth in which microorganisms will rapidly grow. It has been found from experience that some microorganisms will grow much more rapidly in a liquid medium, and such a liquid medium may be located in the bag 184. This bag 184 is also made of any suitable plastic such as a thin polyethylene film. The bag 184 with the agent 186 therein, may be a suitable liquid, even plain water or a simple saline solution if desired, is thus mounted in the interior of the container 150 in the manner illustrated. This bag 184 has an elongated tear strip portion 188 which when removed will release the contents of the bag 184 to the interior of the container 150. This tear strip portion 188 is integrally fixed with an extension 190 which terminates in a thicker portion 192 which surrounds and is fixedly bonded to the plastic filamentary retractor element 174.

When the embodiment of FIG. 14 is introduced into the body cavity the frayed end 182 of the wick 180 which forms the fluid-collecting means will engage the fluid which is to be collected and the fluid will by capillary action be sucked along the wick 180 so as to saturate the latter with the fluid, and this fluid will of course come into engagement with the curved end of element 166 which is formed with the slot 168. This element 166 forms a trigger means which in response to engagement with the collected liquid and/or in response to the temperature in the body softens and gives way either by dissolving or crumpling or the like so as to release the tension in the elastic 162 which at this time will pull the element 164 toward the projection 160 as the elastic band 162 contracts. The result is that the wick 178 as a result of the connection of its portion 180 to the retractor element 174 becomes automatically pulled into the interior of the container 150 after a suitable quantity of fluid has been collected in the latter. In addition, as the retractor portion 174 moves to the right in response to contraction of the elastic band 162, the parts 190 and 192 act to tear the tear strip portion 188 from the bag 184 so as to open the latter and release the agent 186 to the interior of the container so that this agent will now cooperate with the collected fluid for purposes such as preserving the latter, growing microorganisms which may be present in the fluid, or if there is an antibiotic forming at least part of the agent 186 certain undesirable microorganisms, if they are present, will be inhibited by the antibiotic agent.

At the same time, the retraction of the portion 174 by the contraction of the elastic 162 will serve to displace the closure member 176 into engagement with the tapered portion of the opening 152 so as to tightly close this opening and thus prevent any escape of material from the container 150 while at the same time terminating further admission of material to the interior thereof. The container 150 can then of course be removed from the body, although it may be left to remain in the body for a time sufficient for microorganisms, if they are present, to grow under the conditions prevailing in the interior of the body. For convenience of removal the wall 158 of the element 154 can have a pull-string 160 attached thereto.

It is to be noted that with the embodiment of FIG. 14, if upon removal of the device it has the condition shown in FIG. 14, it is immediately known that for some reason the triggering action did not take place and that in fact no fluid was collected, for example because the device was improperly positioned. Therefore, with this device there is an assurance that there will be no false or unnecessary checking for fluid which has not even been collected. If the device is removed and still has the condition shown in FIG. 14, then of course it can be reinserted and properly positioned.

Figure 15:
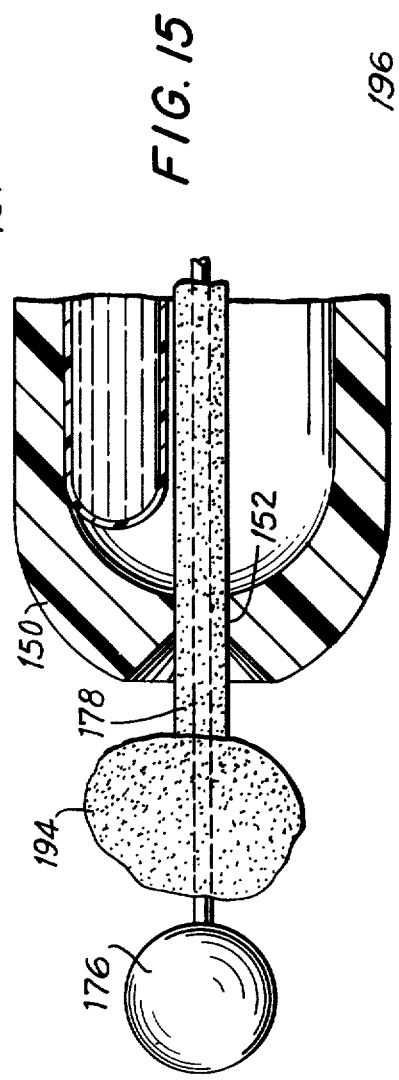
FIG. 15 is a fragmentary illustration of a variation of the embodiment of FIG. 14.

According to the variation of the embodiment of FIG. 14 which is shown in FIG. 15, the wick 178 instead of having a frayed end 182 is connected beyond the container 150 with a ball 194 of cotton or the like which greatly facilitates the collection of the fluid. The ball of cotton 194 is soft enough so that it can be pulled together with the remainder of the wick through the opening 152 in the manner described above, and of course then the closure element 176 will seal the opening 152.

Figure 16:
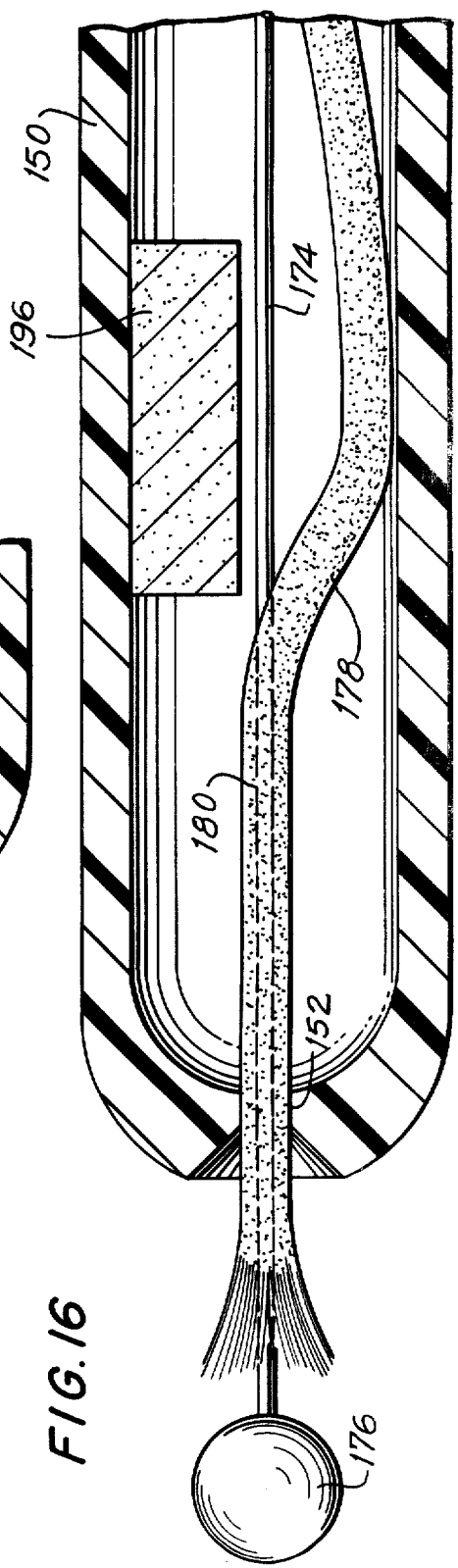
FIG. 16 is a fragmentary schematic sectional view of a still further variation of the embodiment of FIG. 14.

In the embodiment of the invention which is illustrated in FIG. 16, the structure is identical with that of FIG. 14 except that there is no flexible bag 184 with an agent therein. Instead a block 196 is fixed to the inner surface of the container 150 as illustrated. This block 196 is in the form of a relatively solid agar having a nutrient medium, as is well known, for microorganisms which may be present in the collected fluid. It will be noted that the position of the block 196 with respect to the wick 178 is such that when the wick 178 is retracted by the retractor element 174, the portion 180 of the wick will necessarily rub across the block 196 so as to deposit in a highly reliable manner a specimen of fluid on the agar element 196 so that the nutrient in the agar will bring about desired growth and culturing of microorganisms if they are present in the fluid. Thus, by examining the block 196 after a sufficient time it is possible to determine whether or not certain microorganisms are present. For this purpose it may be possible to introduce suitable dyes with a syringe needle through the wall of the container 150 or the latter may simply be broken away to render the block 196 accessible for checking as to whether or not colonies of suspected microorganisms have grown.

It is apparent, therefore, that with the present invention it is possible to situate in a body cavity a structure which while being extremely comfortable at the same time will reliably collect body fluid in such a way that the collected fluid cannot be returned to the body cavity. This collected fluid can be treated in a variety of ways to enable desired information to be derived from the collected body fluid. Also it is possible as was pointed out above to greatly improve the manner in which menstrual blood is collected.

In this latter connection it is to be noted that in accordance with the present invention it is also possible upon removal of a conventional tampon during menstrual flow to squeeze or flush and squeeze the collected menstrual fluid into a container and then send the container to a laboratory or the like so that the collected fluid can be tested. In the alternative it is also possible to place the removed tampon with the collected fluid therein in its entirety in a container for transmittal to a laboratory for testing purposes. In either of these latter embodiments of methods according to the present invention it is possible to situate in the container which receives either the fluid from the tampon or the entire tampon with the fluid therein a suitable preservative such as an antibiotic or the like.

In the above-described embodiments of the invention it is possible to include in any of the above enclosures with the collected fluid not only a suitable preservative such as citric acid or an antibiotic, but in addition it is also possible to include a suitable diluting agent, which in many cases may be water, so that the collected fluid will have a desired concentration suitable for subsequent analysis or for certain functions such as action of an antibiotic or the like.

Of course, it is to be understood that when any of the above embodiments of the invention is removed from a given individual, it is provided with suitable identification so that a specimen which is analyzed can be accurately related to a given individual, thus preventing transmission of information in connection with a specimen to an individual from whom the specimen was not taken. Such identification may be in the form of a suitable adhesive tape or the like which is attached to the exterior of the device and which bears on it identifying indicia such as the name of the individual, an identifying number, or the like.

Furthermore, when a specimen is to be checked it can first be subjected to treatments such as agitation, exposure to ultrasonic waves, centrifuging, filtering or the like, in order to place the specimen in a condition suitable for analysis.

It is to be understood that in the above description and the claims which follow the term "vaginal fluid" is intended to include not only menstrual blood but also any discharge which may be collected in the vagina, such as discharges which may be received at the cervix from the uterus, or mucous or other fluids found in the vagina and capable of being tested to indicate vaginitis. As is well known, the discharges such as menstrual blood will include endometrium and the tests which are carried out during analysis may be used to indicate the presence or absence of diseases such as gonorrhea or cancer. Thus, the term "vaginal fluid" is intended to include all such materials, even solid particles which are suspended in the collected fluid, while "menstrual blood" is intended to signify not only blood per se but rather the entire discharge during menses, including endometrium, cells, microorganisms, mucous, etc.

Particularly in the case of menstrual blood, one of the important treatments according to the present invention in connection with analysis resides in diluting the menstrual blood with a suitable amount of water so that the red blood cells previously suspended in the menstrual blood will settle after expansion, as is well known with other blood taken from the body of a human being, animal, or the like. It has been found that when menstrual blood is diluted in this way, after the red blood cells have settled the solution still has suspended therein all other cells, microorganisms, particles, and the like such as endometrium particles, cancer cells, etc. Thus, by treating menstrual blood in this way it is possible to obtain very easily a solution from which a part may be removed and placed on a slide for suitable examination under a microscope, for example. Thus, by diluting menstrual blood with a suitable amount of water it is possible to obtain in the solution which has no red blood cells therein in a highly convenient manner a specimen suitable for analysis for presence or absence of certain diseases as pointed out above.

It is at the present time known to take a smear from the cervix or other areas accessible in the vagina and to check such a specimen for the presence or absence of certain diseases. These procedures, however, involve a certain amount of inconvenience in that the specimen must be placed on a suitable slide, and then it must be dried, it must have suitable dyes applied thereto, and then when situated between a pair of slides it is examined under a microscope. In connection with the well known Pap test for cancer, some 30 different steps are required in order to determine the presence or absence of cancer.

It has been found most surprisingly in accordance with the present invention that procedures of this type can be considerably simplified because the solution which remains after the red blood cells of the menstrual blood have settled out of the solution is extremely rich in endometriun and cells which may be cancer cells. For example, according to the invention in one specific procedure 2 cc of menstrual blood are diluted with 4 cc of distilled water, at room temperature, and after some slight agitation, the solution is allowed to stand for a period of only 5 minutes, after which the red blood cells settle to the bottom of the solution. The liquid which remains is extremely rich in cells which may possibly be cancer cells, and as a result of this fact it is possible to greatly simplify presently known procedures for detection of uterine cancer. Thus, a part of this remaining liquid may be applied as a film to a slide and treated in a conventional manner for detection of presence or absence of cancer cells. However it is also possible simply to filter the liquid remaining after the red blood cells of the menstrual blood have settled out of the solution. Through such filtering it is possible to collect a mass of matter in which cancer cells, for example, if they are present will be present in such numbers that by utilizing dyes which are normally used for conventional detection of the presence or absence of cancer cells it is possible to provide the mass remaining after filtration with a suitable dye so that simply by inspecting the color of this remaining mass or the color of a solution into which the dyed material has been placed it is possible to detect the absence or presence of cancer without the presently known complications. Of course the material remaining after filtration can, if desired, first be placed into a solution and then such a solution may be provided with a suitable dye so that if cancer cells are present they will in a known way provide an indication by color of the presence of absence of cancer.

Procedures of this type particularly in connection with a solution from emdometrium or cervix cells contained in the liquid remaining after the red blood cells have settled makes it possible to utilize automatic procedures for detecting the presence or absence of uterine cancer. For example either part of the solution remaining after settling of the red blood cells from the menstrual blood or the matter which has been filtered from the solution and itself placed in the solution can be treated with a suitable dye, and thereafter the liquid can be processed through known devices for automatically detecting the presence or absence of certain colors in a highly accurate manner so that through such automatic procedures the presence or absence of cancer can be detected. For example there are known colorimeters in which light passing through a suitable optical system is also passed through the solution which is to be tested, with suitable photocells or the like responding to given wave lengths so as to pick up in a highly accurate manner signals which are processed for indicating automatically whether or not certain colors indicative of the presence or absence of certain diseases are present. Such devices can be used with the materials derived from the menstrual blood in accordance with the present invention so as to detect the presence or absence of uterine cancer in a manner which is far more efficient and less costly than presently known methods.

In connection with preservatives in the form of antibiotics which can be utilized either before or after fluid collection, it is to be noted that a solid preservative can be utilized. Such a solid, chloramphenicol for example, can be situated in the container in which fluid is to be collected prior to fluid collection so that only upon contact by the collected liquid will the solid preservative dissolve to provide the preservative action. However it is also possible to introduce such a solid antibiotic substance, in suitable pellet form, for example, into the collected fluid after it is collected, as, for example, into the container in which the collected fluid is transmitted to a laboratory or the like for analysis.

It is to be noted that, as is apparent from the above description, according to the present invention a noninvasive collection system is utilized in that according to the invention there is no interference with normal body functions and no procedures such as scraping or the like to remove tissue are involved.

Also, in connection with the above description it is to be noted that the term "microorganisms" is intended to include bacteria, fungi, and viruses, without necessarily being restricted only to the latter types of microorganisms.

What is claimed is:

1. In a method for obtaining information pertaining to human beings or other animals having body cavities wherein fluids from which the desired information can be derived are at least temporarily present, the steps of situating at a body cavity a means responding to presence of a fluid at the body cavity for collecting the fluid, leaving the latter means at the body cavity for a length of time sufficient to provide for collection of a quantity of fluids suitable for subsequent analysis, enclosing the collected fluid while said means remains in the body cavity in an enclosure suitable for transmittal to a laboratory or the like where the collected fluid is to be analyzed, while preventing the collected fluid in said enclosure from flowing out of said enclosure, and then analyzing the body fluid to obtain the desired information.

2. In a method as recited in claim 1 and wherein an enclosure having an entrance through which fluid enters the enclosure is situated at the body cavity with said entrance forming the means for collecting the body fluid while the remainder of the enclosure serves to enclose the collected fluid in the body cavity.

3. In a method as recited in claim 1, said enclosure having an entrance through which fluid enters the enclosure, and including the step of closing said entrance after a suitable quantity of the body fluid has been collected in said enclosure.

4. In a method as recited in claim 3 and wherein the closing step in manually performed.

5. In a method as recited in claim 3 and wherein the closing step is automatically performed.

6. In a method as recited in claim 1 and wherein the means situated at the body cavity to collect the body fluid is in the form of a unit capable of absorbing a body fluid by capillary action.

7. In a method as recited in claim 6 and wherein the enclosure for enclosing the body fluid is situated at the body cavity together with said unit with the latter extending partly into the enclosure.

8. In a method as recited in claim 7 and wherein said unit is compressible to squeeze body fluid therefrom while said enclosure is at least in part flexible at a portion surrounding said unit between a part thereof situated outside of the enclosure and a part thereof situated within the enclosure, and including the steps of contracting the flexible part of the enclosure to squeeze the unit at the part thereof which extends through the contracted enclosure part, and while maintaining the flexible part of the enclosure in its contracted condition withdrawing the unit from the enclosure to squeeze the fluid out of the unit into the enclosure.

9. In a method as recited in claim 6 and wherein said unit extends only partly into the container so that the fluid drips from the unit into the container in a hollow portion thereof situated beyond the unit.

10. In a method as recited in claim 1 and wherein said agent is a preservative applied to the collected body fluid prior to analysis of the body fluid.

11. In a method as recited in claim 10 and wherein the preservative is an antibiotic.

12. In a method as recited in claim 10 and wherein a part of the body fluid which is to be analyzed is extracted from the body fluid prior to said analysis.

13. In a method as recited in claim 12 and wherein the extracted part of the body fluid is diluted in a suitable solution prior to analysis.

14. In a method as recited in claim 1 and wherein the body cavity is the vagina and the collected fluid is menstrual blood.

15. In a method as recited in claim 14 and wherein the menstrual blood is diluted with water to precipitate red blood cells therefrom.

16. In a method as recited in claim 15 and wherein the solution remaining after precipitation of the red blood cells from the menstrual blood is tested for presence of uterine cancer cells and other cells of the female reproductive tract.

17. In a method as recited in claim 16 and wherein the matter suspended in the solution after precipitation of the red blood cells is separated from the solution and is then tested for the presence of uterine cancer cells and other cells of the female reproductive tract.

18. In a method as recited in claim 1 and including the step of situating in the enclosure said agent which will give the collected fluid a predetermined condition.

19. In a method as recited in claim 1 and including the step of applying part of the collected fluid to a growth medium situated in the enclosure, so that growth of bacteria or the like in the fluid can go forward even during transmittal of the enclosure to the laboratory or the like for subsequent analysis.

20. In a method for obtaining information pertaining to human beings or other aminals having body cavities wherein fluids from which the desired information can be derived are at least temporarily present, the steps of situating at a body cavity a means for collecting a body fluid present at the cavity, leaving the latter means at the body cavity for a length of time sufficient to provide for collection of a quantity of the fluid suitable for subsequent analysis, enclosing the thus-collected fluid in an enclosure suitable for transmittal to a laboratory or the like where the collected fluid is to be analyzed, and then analyzing the body fluid to obtain the desired information, and including the step of automatically closing the enclosure after a suitable quantity of fluid has been collected therein and simultaneously with the closing step releasing to the interior of the enclosure an agent which will contact the fluid collected therein to give the fluid a predetermined condition.

21. In a method as recited in claim 20 and wherein the released agent is a broth for promoting the growth of bacteria in the collected fluid.

22. In a method as recited in claim 1 and wherein the means for collecting the body fluid is a tampon and the body cavity being a vagina into which the tampon is introduced for collecting vaginal fluid, and the enclosure being outside of the body and including the step of transferring fluid from the tampon to the enclosure for transmittal therein to a laboratory or the like.

23. In a method as recited in claim 22 and wherein a preservative is also introduced into the enclosure.

24. In a method as recited in claim 23 and wherein the enclosure is provided with suitable identification of the individual from whom the fluid is derived.

25. In a method as recited in claim 24 and wherein the material in the enclosure is subjected to treatments such as agitation, exposure to ultrasonic waves, centrifuging, or the like.

* * * * *